United States Patent
Hopkins et al.

(10) Patent No.: US 8,608,862 B2
(45) Date of Patent: Dec. 17, 2013

(54) CLEAN IN PLACE GASSING MANIFOLD

(75) Inventors: Jerry Hopkins, Omaha, NE (US); Kevin G. Mellor, Kennewick, WA (US)

(73) Assignee: ConAgra Foods RDM, Inc., Omaha, NE (US)

( * ) Notice: Subject to any disclaimer, the term of this patent is extended or adjusted under 35 U.S.C. 154(b) by 407 days.

(21) Appl. No.: 12/966,759

(22) Filed: Dec. 13, 2010

(65) Prior Publication Data

US 2011/0083704 A1 Apr. 14, 2011

Related U.S. Application Data

(62) Division of application No. 11/894,250, filed on Aug. 20, 2007, now Pat. No. 7,850,788.

(51) Int. Cl.
*B08B 9/20* (2006.01)

(52) U.S. Cl.
USPC ............. 134/22.1; 134/22.18; 134/34; 141/1; 141/89; 141/91

(58) Field of Classification Search
USPC .......... 134/22.1, 22.18, 34, 37, 42; 141/1, 89, 141/90, 91
See application file for complete search history.

(56) References Cited

U.S. PATENT DOCUMENTS

| | | | |
|---|---|---|---|
| 3,970,584 A | 7/1976 | Hart et al. | 252/305 |
| 4,339,111 A | 7/1982 | Welch | 251/331 |
| 4,396,044 A * | 8/1983 | Ahlers | 141/90 |
| 4,579,156 A | 4/1986 | Graffin | 141/89 |
| 4,856,684 A | 8/1989 | Gerstung | 222/402.23 |
| 4,940,171 A | 7/1990 | Gilroy | 222/402.18 |
| 4,958,755 A | 9/1990 | Gerstung | 222/402.23 |
| 4,964,444 A * | 10/1990 | Hanerus et al. | 141/90 |
| 5,073,206 A | 12/1991 | Wilson et al. | 134/40 |
| 5,143,260 A | 9/1992 | Loychuk | 222/95 |
| 5,531,253 A | 7/1996 | Nishiyama et al. | 141/90 |
| 5,740,844 A | 4/1998 | Miller | 141/90 |
| 5,810,059 A | 9/1998 | Rutter et al. | 141/92 |
| 5,836,364 A | 11/1998 | Burton | 141/348 |
| 5,891,260 A | 4/1999 | Streets et al. | 134/8 |
| 6,253,811 B1 | 7/2001 | Slagh | 141/383 |
| 6,287,515 B1 | 9/2001 | Koosman et al. | 422/22 |
| 7,037,550 B2 | 5/2006 | Liu et al. | 426/609 |
| 7,850,788 B2 | 12/2010 | Hopkins et al. | 134/166 R |

FOREIGN PATENT DOCUMENTS

| | | | |
|---|---|---|---|
| GB | 1103081 | | 2/1968 |
| WO | 91/01258 | | 2/1991 |
| WO | WO2007/019590 | * | 2/2007 |

* cited by examiner

*Primary Examiner* — Saeed T Chaudhry
(74) *Attorney, Agent, or Firm* — Advent, LLP; Ryan T. Grace

(57) ABSTRACT

A method for cleaning a gassing manifold includes providing a gassing module and a complementary clean in place module for coupling to the gassing module. Cleaning solution is pumped from the clean in place module to the gassing module above a minimum flow rate and velocity for effective cleaning.

20 Claims, 12 Drawing Sheets

CLEAN IN PLACE GASSING MANIFOLD

CROSS-REFERENCE

The present application is a divisional of U.S. patent application Ser. No. 11/894,250, filed Aug. 20, 2007, which is herein incorporated by reference in its entirety.

TECHNICAL FIELD

The disclosure generally relates to the field of automatic filling systems and more particularly to a clean in place gassing manifold for an automatic filling system for a food product distributed in a pressurized spray can, such as whipped cream.

BACKGROUND

Small, economical containers are used in large volume for the storage, transportation, and dispensing of food products. A commonly utilized container is the pressurized spray can. Generally, an automatic filling system receives a succession of empty cans by some conveying means for filling products. The automatic filling system has a food filling nozzle and/or manifold that fills the spray cans with food. The automatic filling system may also utilize a gassing nozzle and/or manifold to insert propellant into the food filled spray cans to pressurize the cans. Whipped cream, spray oil, and processed cheese may be stored and dispensed utilizing pressurized cans. It is necessary to thoroughly clean the hoses, pipes, and other parts of the gassing manifold's product and propellant delivery system to disinfect food contact surfaces to prevent the growth of potentially harmful microorganisms.

In order to clean the gassing manifold of an automatic filling system, it is necessary to disassemble substantial portions of the gassing manifold prior to cleaning. This disassembly may be time consuming and labor intensive. Furthermore, hard to reach surfaces of the manifold could be missed during cleaning.

SUMMARY

Accordingly, the disclosure is directed to a clean in place gassing manifold, to a method for providing a clean in place gassing manifold, and to a method for cleaning a gassing manifold.

The clean in place gassing manifold comprises a gassing module comprising a hub, the gassing module and the hub being formed as a unitary device; and a complementary clean in place module for coupling the gassing module, the complementary clean in place module comprising a head that inserts into the hub of the gassing module. The gassing module coupled with the complementary clean in place module allow a cleaning solution to be pumped through the coupled modules at and above a minimum flow rate and a minimum velocity for effective cleaning The method for providing a clean in place gassing manifold comprises providing a gassing module comprising a hub, the gassing module and the hub being formed as a unitary device, and providing a complementary clean in place module for coupling the gassing module, the complementary clean in place module comprising a head that inserts into the hub of the gassing module. The gassing module coupled with the complementary clean in place module allows a cleaning solution to be pumped through the coupled modules at and above a minimum flow rate and a minimum velocity for effective cleaning.

The method for cleaning a gassing manifold comprises inserting a clean in place module into a gassing module to form a coupled module, pumping a cleaning solution through the coupled module, and removing the clean in place module from the gassing module. The coupled module allows the cleaning solution to be pumped through the coupled module at and above a minimum flow rate and a minimum velocity for effective cleaning It is to be understood that both the foregoing general description and the following detailed description are exemplary and explanatory only. The accompanying drawings, which are incorporated in and constitute a part of the specification, illustrate examples and together with the general description, serve to explain the principles of the disclosure.

BRIEF DESCRIPTION OF THE DRAWINGS

The numerous advantages of the disclosure may be better understood by those skilled in the art by reference to the accompanying figures in which.

DETAILED DESCRIPTION

Referring generally to FIGS. 1 through 11, a clean in place gassing manifold 100 of an automatic filling system is shown. A CIP gassing manifold 100 may comprise two modules: a gassing module 102 and a clean in place (CIP) module 116. Additionally, the CIP gassing manifold 100 may comprise a spray can delivery system 128. A clean in place system automatically cleans a machine's pipes, orifices, hoses, and other surfaces that may contact food with minimal manual labor by the circulation and/or flowing of chemical detergents, solvents, water rinses, and/or other suitable cleaners for food machines to safely produce food products for human consumption based on microorganism growth.

A clean in place system eliminates the potential for human error when cleaning, the need to pay manual labor for cleaning, and the possibility of exposure to potentially harmful microorganisms for manual cleaners. Therefore, clean in place systems are more efficient, less labor intensive, less expensive, and more consistent than manual cleaning methods.

In order for a clean in place system to work effectively, the cleaning solution pumped through the machine must maintain a minimum flow rate and minimum velocity, which vary based on pipe and tube diameters, to guarantee the cleaning solution contacts the surfaces of the machine that may come into contact with food. Therefore, being able to achieve and/or exceed a minimum flow rate and minimum velocity for the cleaning solution of the clean in place system is needed for an effective clean in place system.

Figure 1:
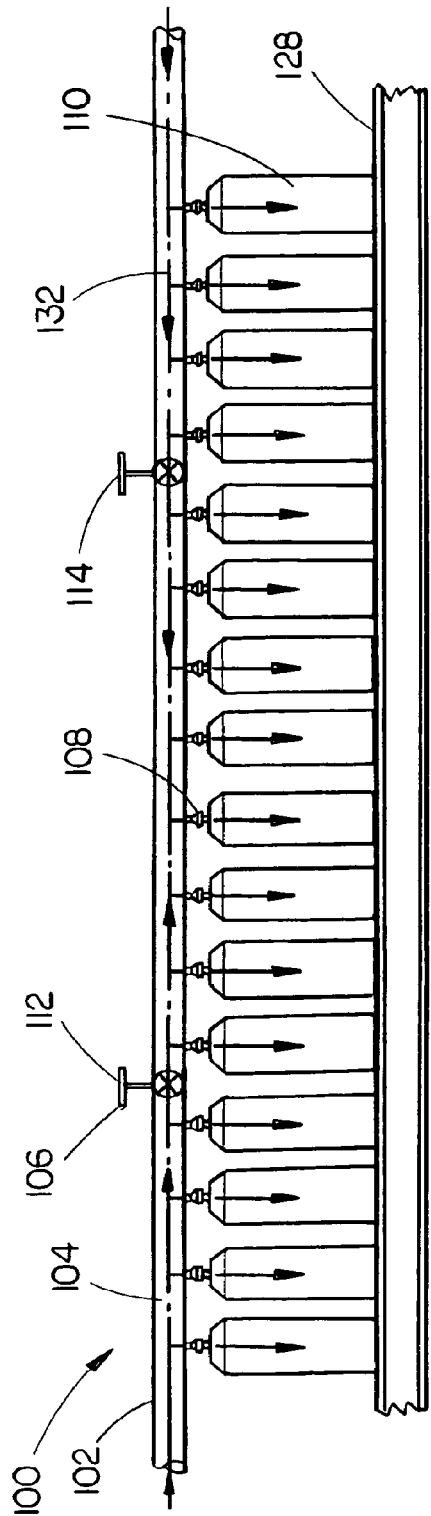
FIG. 1 is a partial front view illustrating a clean in place gassing manifold, wherein a gassing module is coupled with a spray can delivery system.
Figure 2:
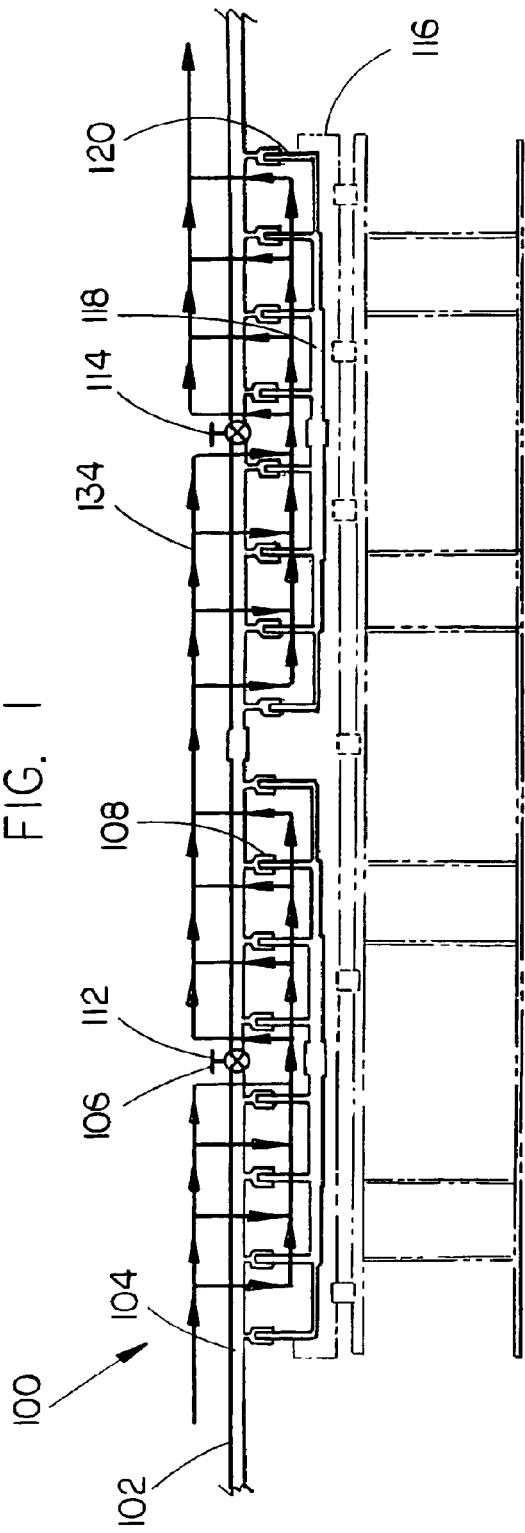
FIG. 2 is a partial side view illustrating a clean in place gassing manifold, wherein a gassing module is coupled with a clean in place module.
Figure 3:
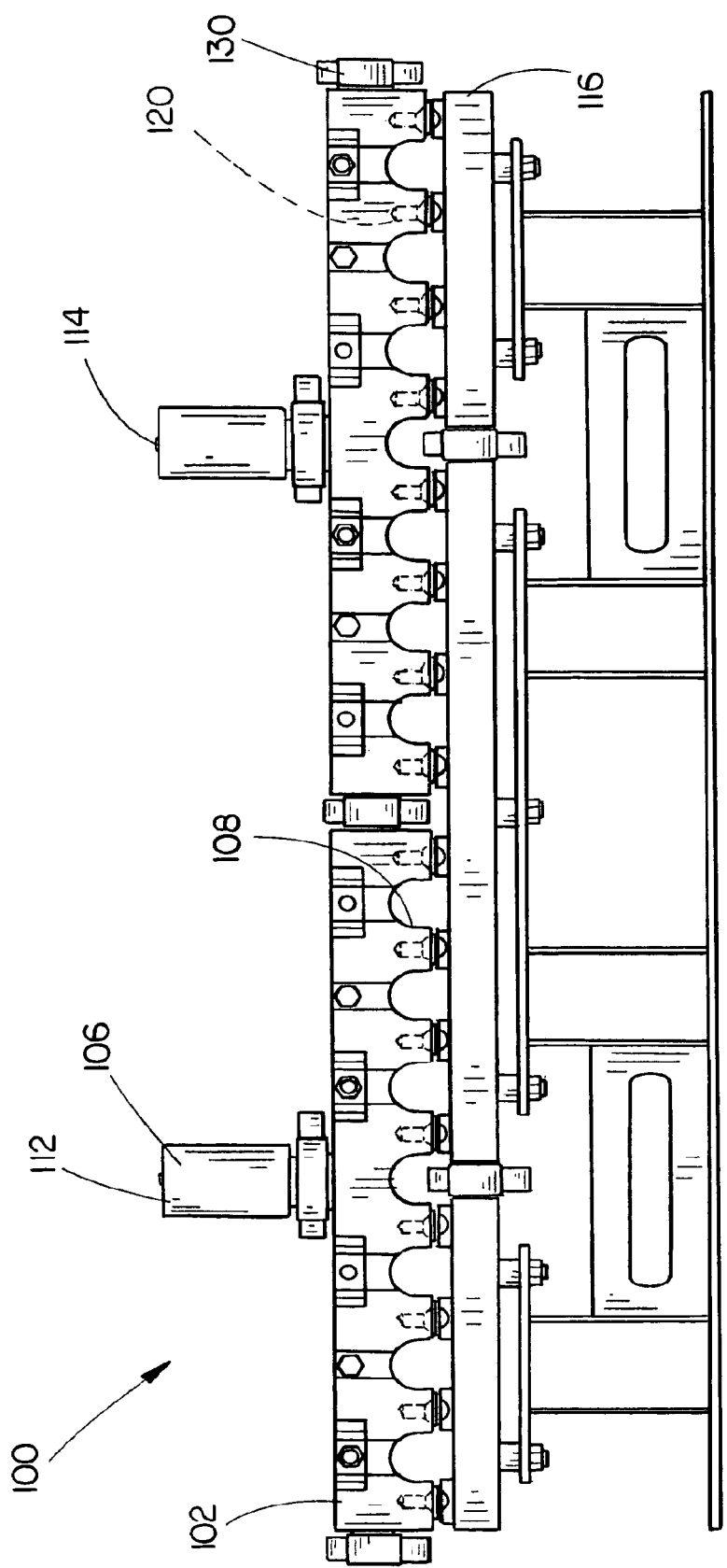
FIG. 3 is a partial side view illustrating a clean in place gassing manifold, wherein a gassing module is coupled with a clean in place module.
Figure 4:
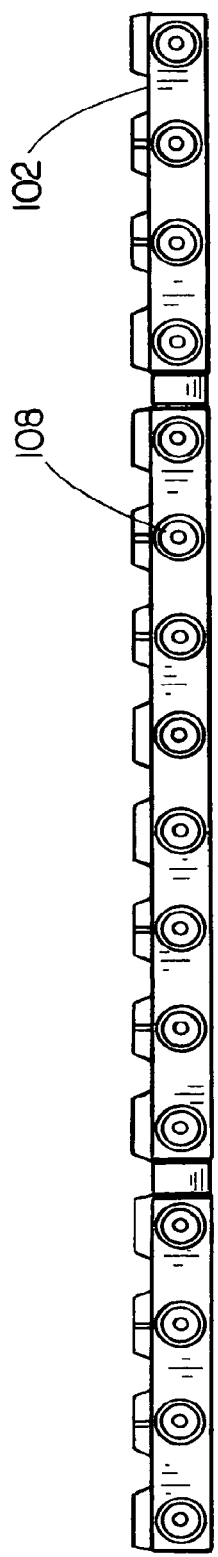
FIG. 4 is a bottom view of the gassing module as illustrated in FIG. 3.
Figure 5:
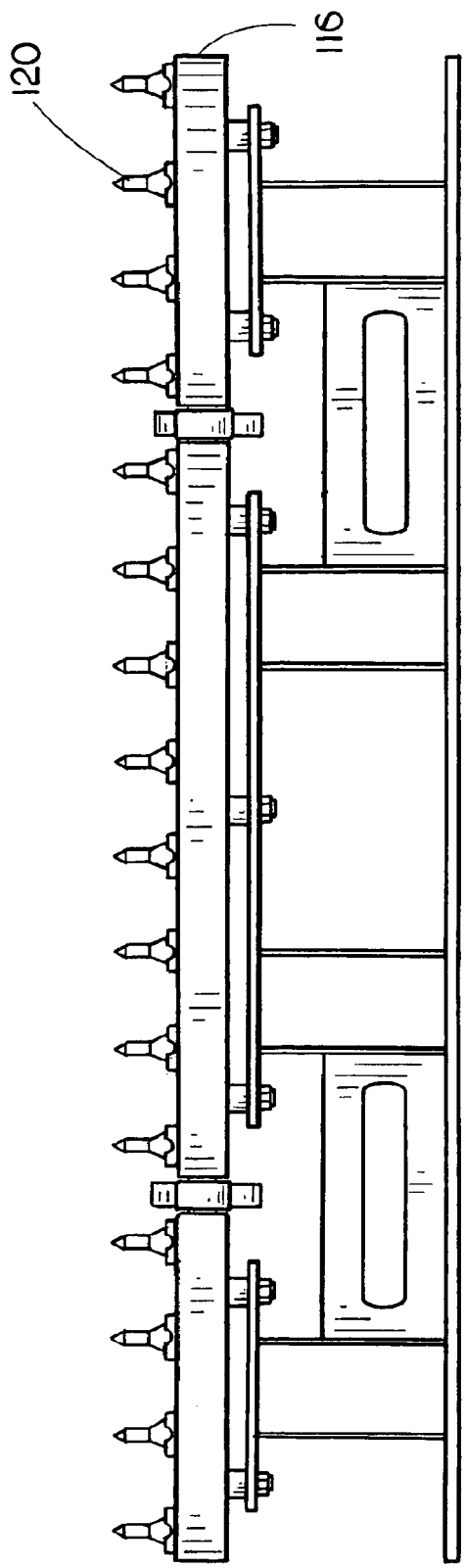
FIG. 5 is a side view of the clean in place module illustrated in FIG. 3.
Figure 6:
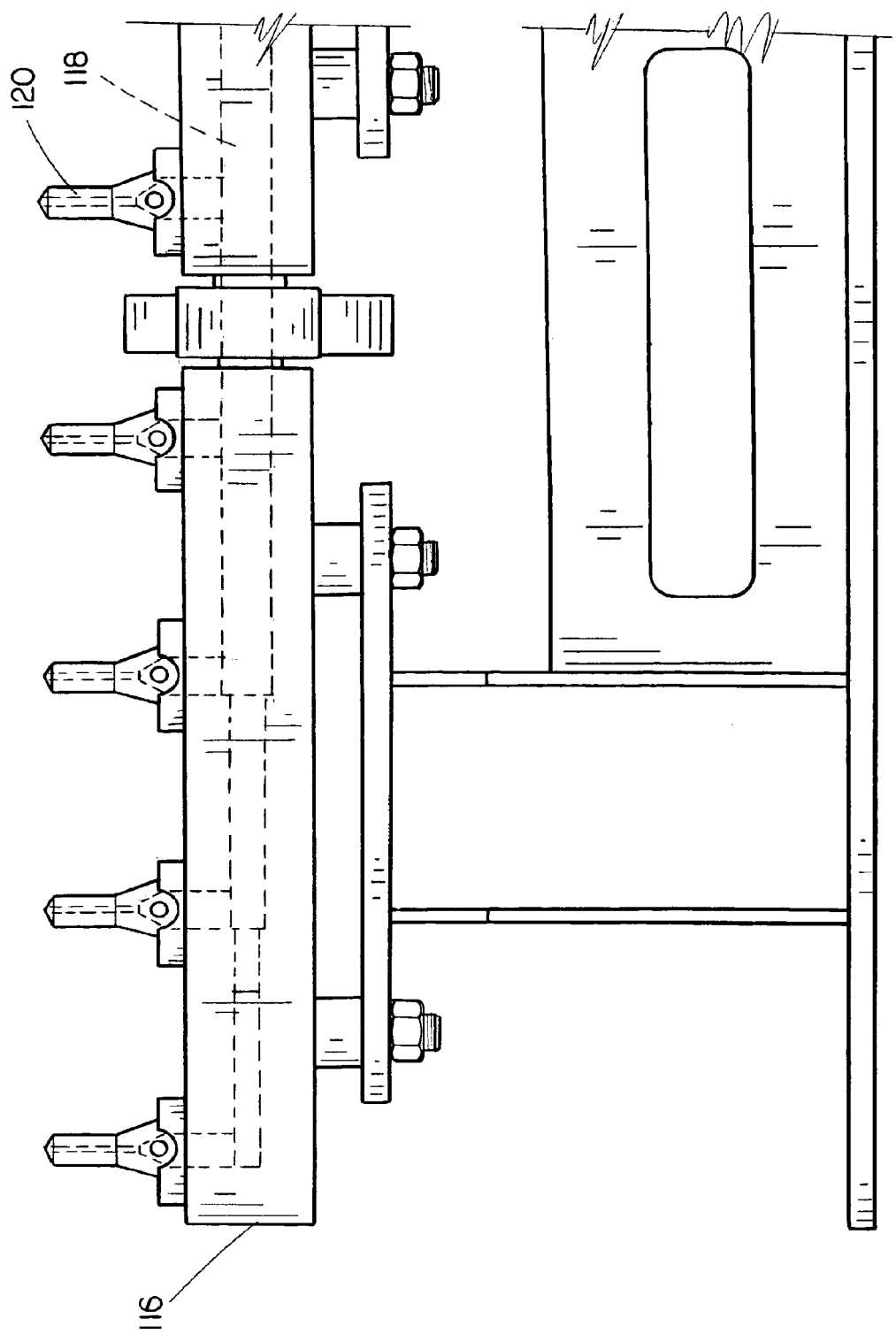
FIG. 6 is a partial side view of the clean in place module illustrated in FIG. 5.
Figure 7:
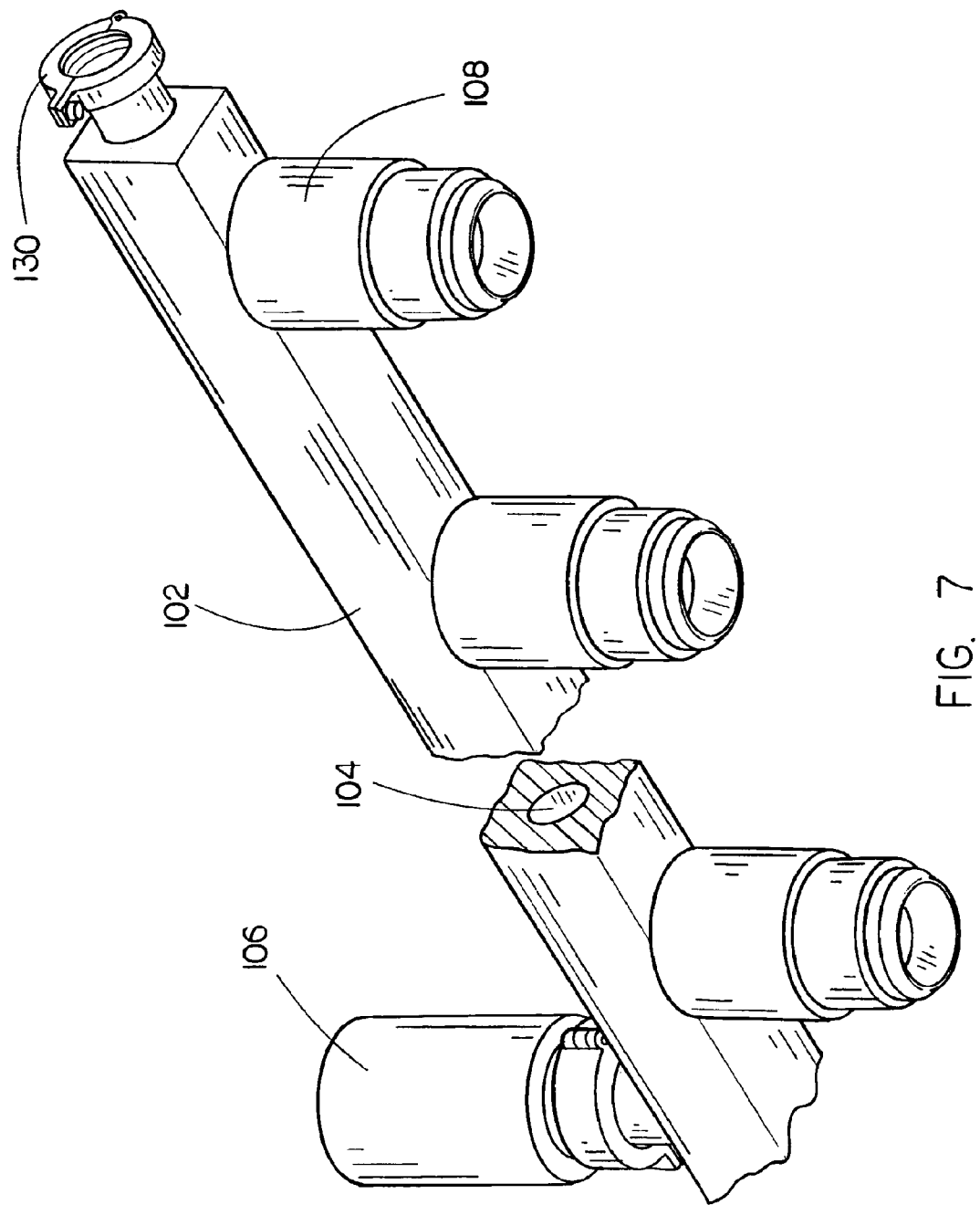
FIG. 7 is a partial isometric view of the gassing module illustrated in FIG. 3.

The gassing module 102 includes a flow tube 104, a valve 106, and a hub 108 as illustrated in FIGS. 1 through 4, 7, and 8. The gassing module 102 may include two valves 112 and 114 and sixteen hubs 108 as illustrated in FIGS. 1 through 3. The hub 108 is not detachable from the gassing module 102 and the gassing module's flow tube 104. The hub 108 and gassing module 102 is a unitary device including a flow tube fixedly connected to one or more hubs, unlike other gassing modules that have detachable/separately added hubs. Typically, detachable hubs are attached with screws, creating crevasses and threads that need to be cleaned thoroughly to prevent potentially harmful microorganisms from growing. Cleaning is only effective for these types of hubs when the entire hub is removed for cleaning, so the threads and crevasses may be reached. Detachable/separate hubs often prevent effective clean in place systems from being created. Because the hubs 108 are part of one continuous structure with the flow tube 104 of the gassing module 102 as illustrated in FIG. 3, there are no crevasses or threads that need to be cleaned, eliminating the need to detach the hub for proper cleaning. This continuous structure is different from other continuous structures by maintaining proper flow areas to maintain CIP velocities and provide consistent gas filling. Moreover, the gassing module may include at least one rotary hub. Furthermore, the gassing module may be a rotary gassing module 102.

The spray can delivery system 128 holds and positions spray cans 110 so that the nozzles of the spray cans 110 may be directly inserted into the hubs 108 of the gassing module 102 as illustrated in FIG. 1. The spray can delivery system 128 holds the same number of spray cans 110 under the gassing module 102 as there are hubs 108 with the nozzles of the spray cans 110 at about the same distance apart as the hubs 108 on the gassing module 102. The spray can delivery system 128 lines up spray cans underneath the gassing module 102 so that every hub 108 may have the nozzle of a spray can 110 held by the spray can delivery system 128 inserted into it automatically by the gassing module 102 of the CIP gassing manifold 100.

Figure 8:
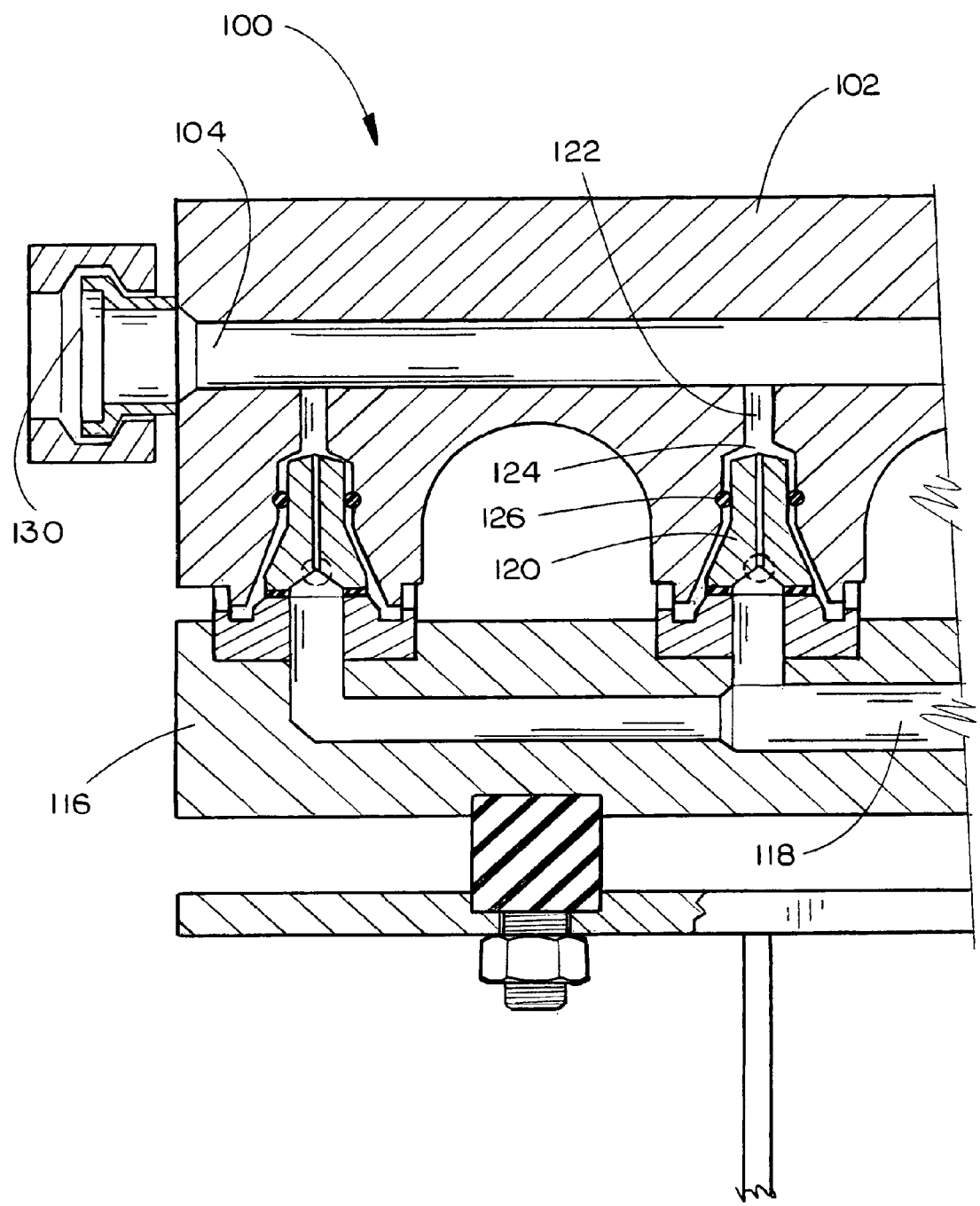
FIG. 8 is a partial cross-sectional side view of the gassing module coupled with the clean in place module as illustrated in FIG. 3.

Similarly, the clean in place module 116 compliments the gassing module 102. The CIP module has receptacle tubes 118 with heads 120 that may be inserted into the hubs 108. In other words, the number of heads 120 and their distances apart on the clean in place module 116 correlate with the number of hubs 108 and their distances apart on the gassing module 102 allowing the heads 120 to be inserted into the hubs 108 of the gassing module 102 automatically by the CIP module 116 of the CIP gassing manifold 100 as illustrated in FIGS. 2, 3, and 8.

Figure 9:
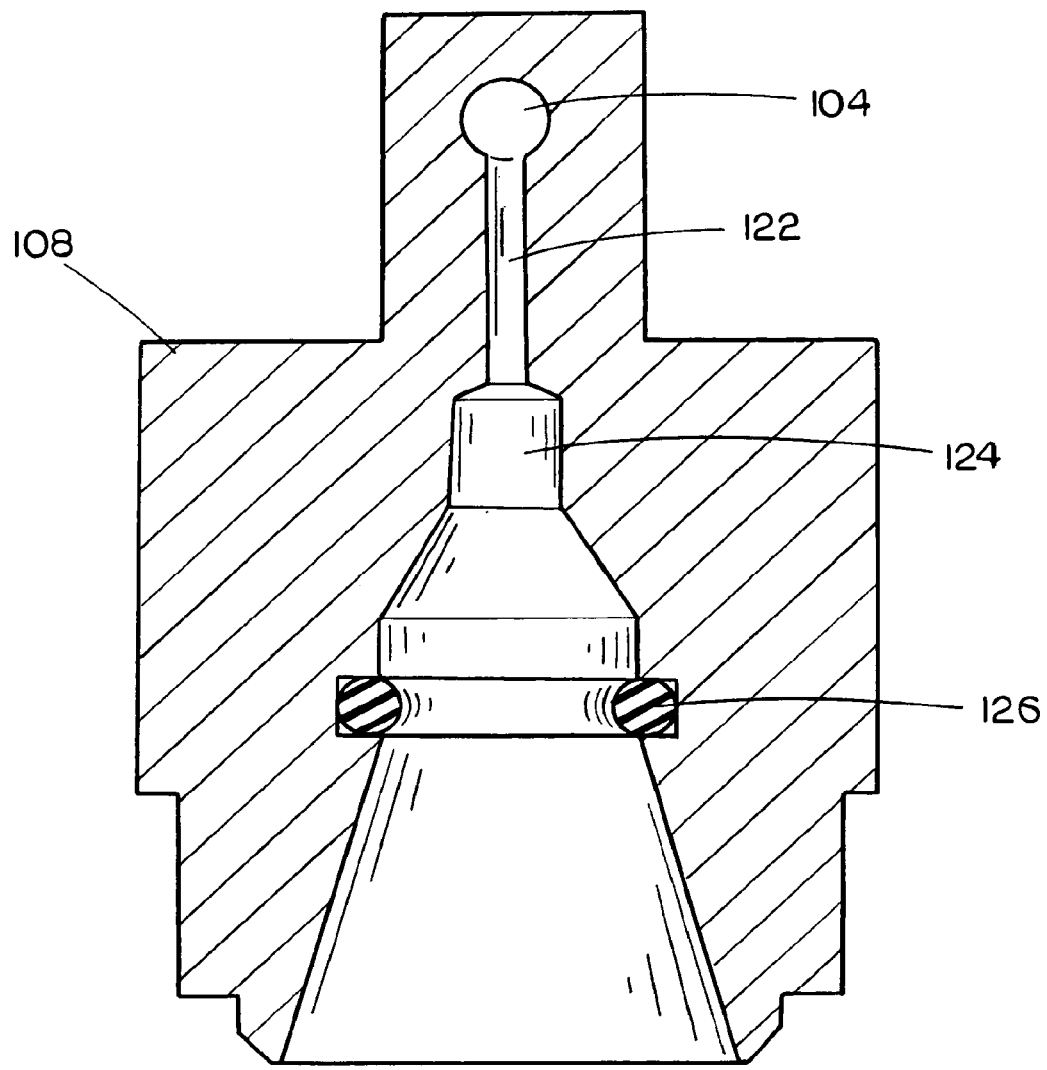
FIG. 9 is a cross-sectional side view of the hub as illustrated in FIG.7.
Figure 10:
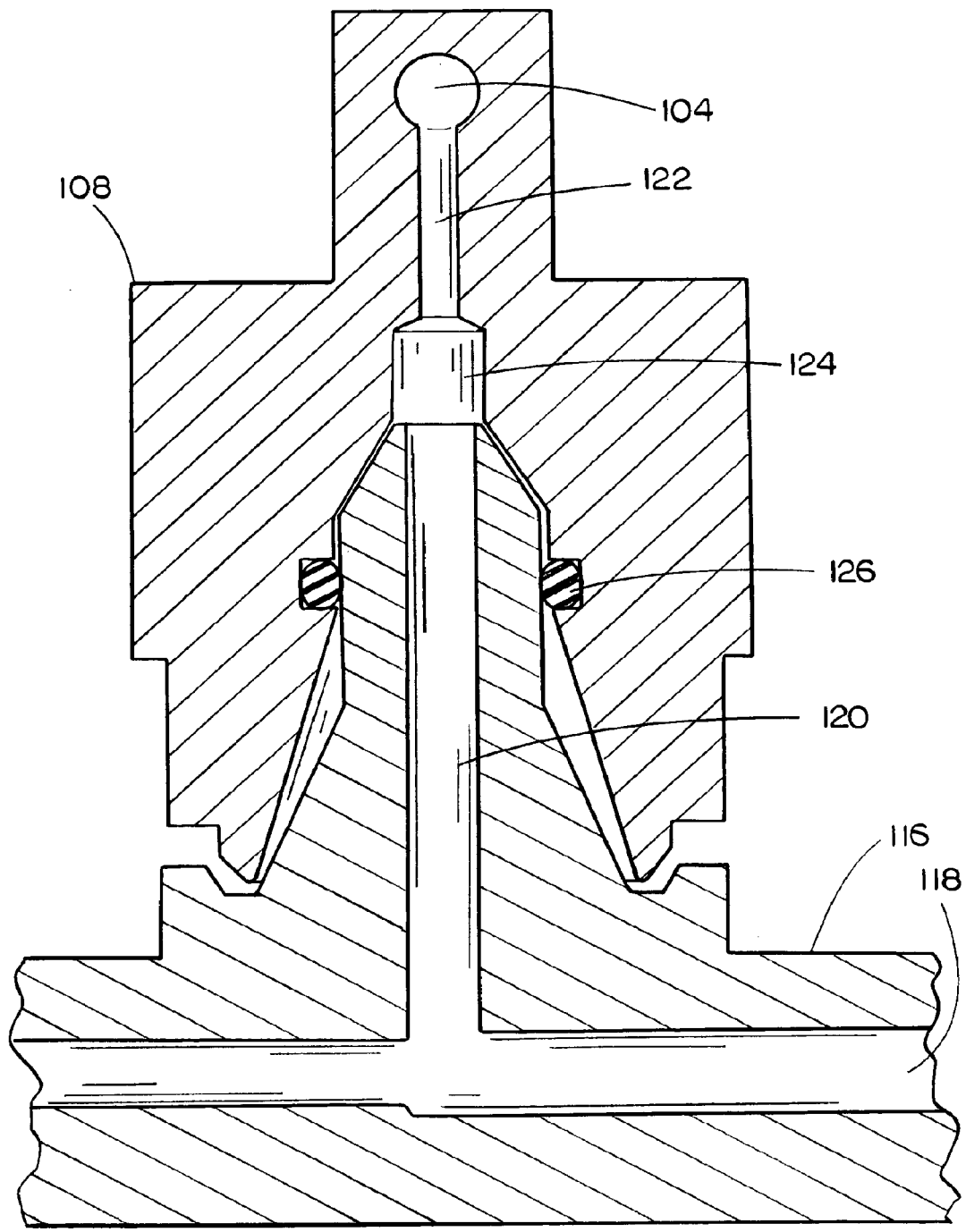
FIG. 10 is a partial cross-sectional side view of the hub coupled with the clean in place manifold as illustrated in FIG. 3.
Figure 11:
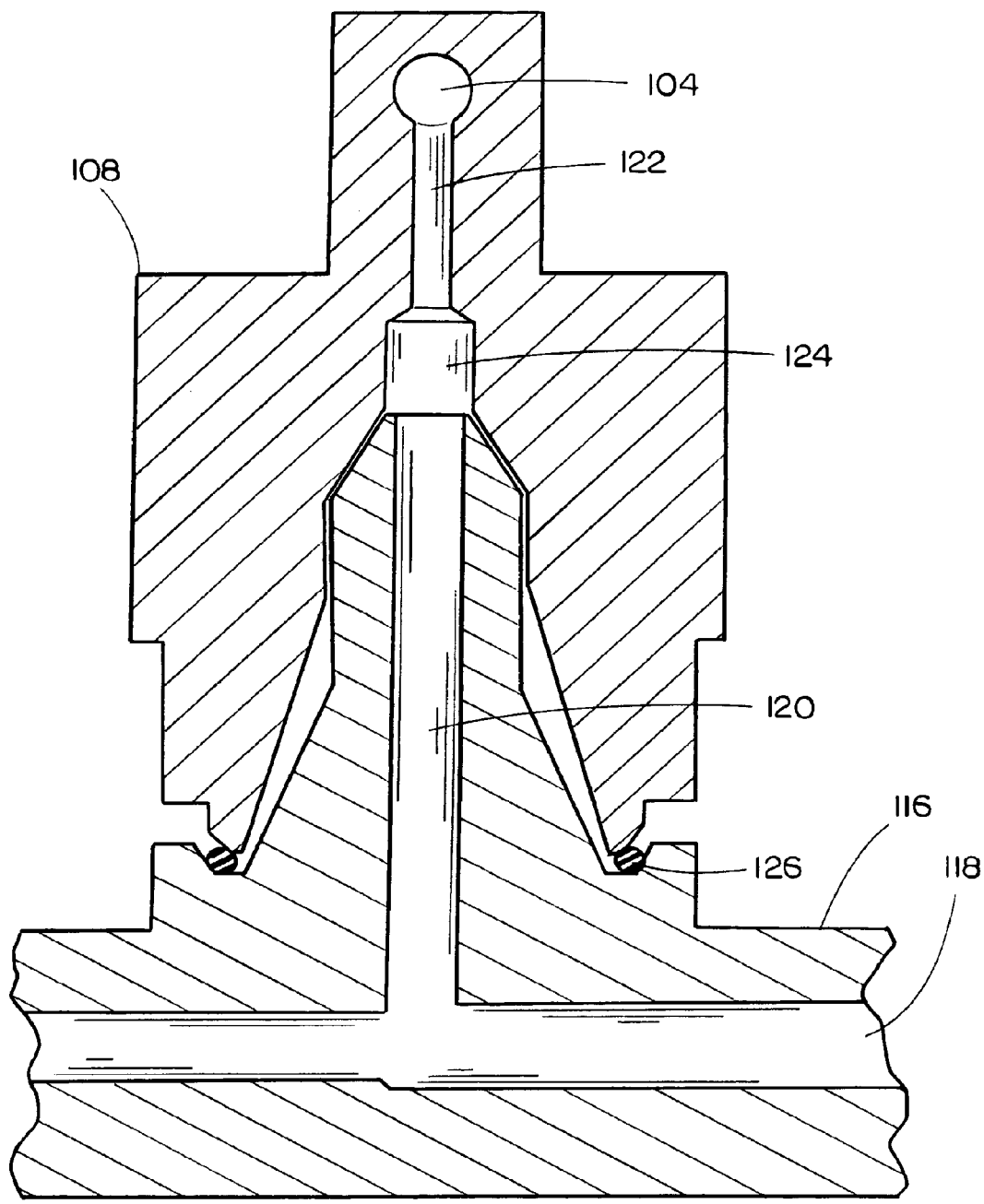
FIG. 11 is a partial cross-sectional side view of a hub coupled with the clean in place manifold, wherein an O-ring is located at the base of the hub.
Figure 12:
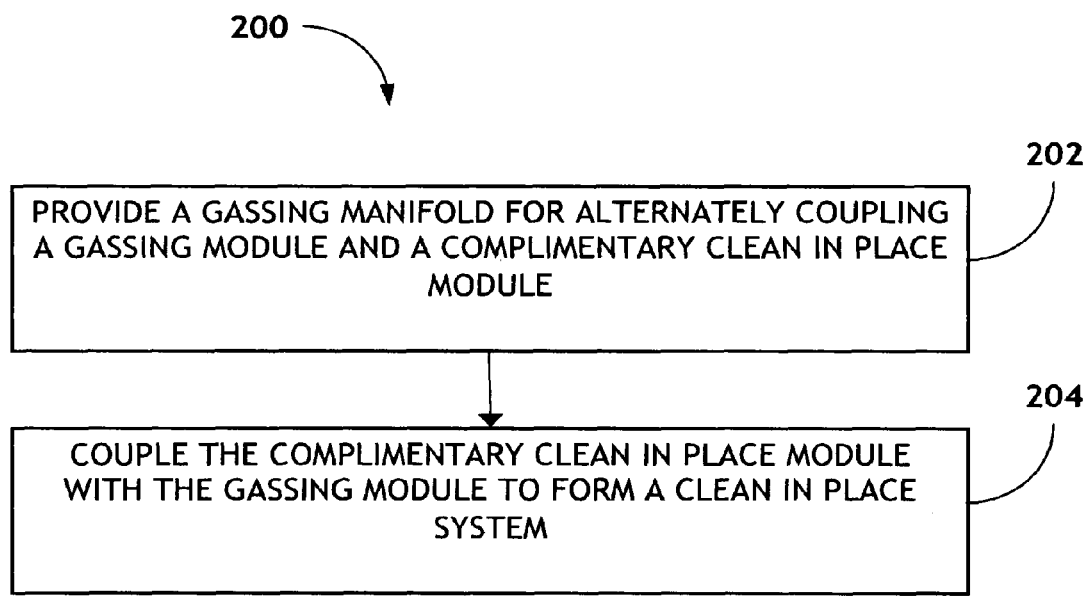
FIG. 12 is a diagram illustrating a method for producing a clean in place gassing manifold.
Figure 13:
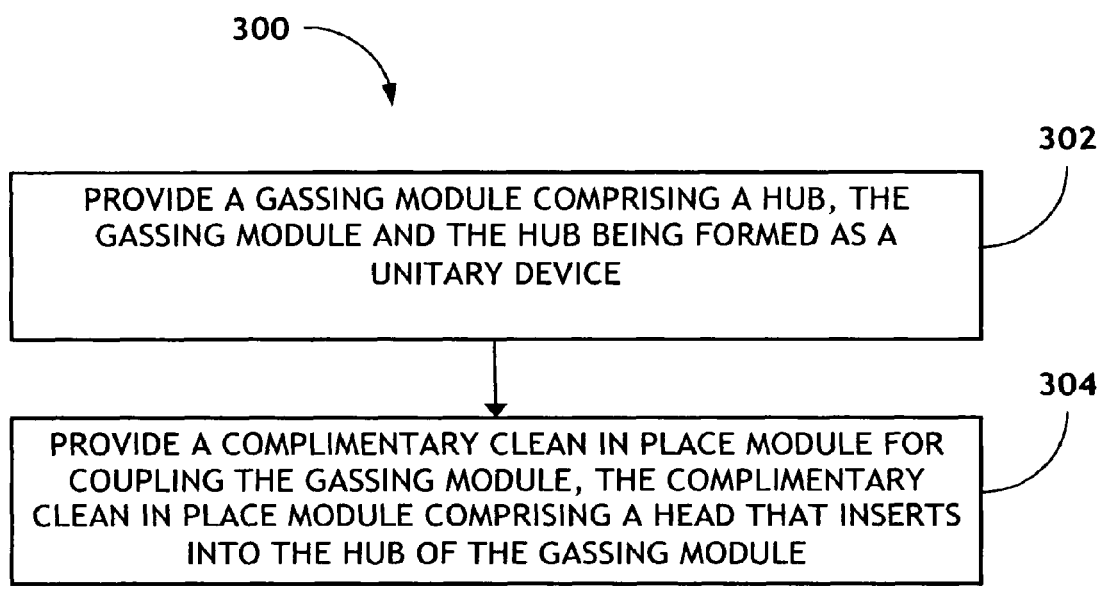
FIG. 13 is a diagram illustrating a method for producing a clean in place gassing manifold.

A hub conduit 122 and hub gap 124 within the hub 108 may connect the flow tube 104 to the nozzles of the spray cans 110 held by the spray can manifold 128 and to the heads 120 of the CIP module 116. An O-ring 126 may seal the hub gap 124 with the nozzles of the spray cans 110 or with the heads 120 of the clean in place module 116 as illustrated in FIGS. 8, 10, and 11. The O-ring 126 may be located in various positions in the hub 108 to seal the hub gap 124 with the nozzles of the spray cans 110 or with the heads 120 of the clean in place module 116. The O-ring may be located near the middle of the hub 108 as illustrated in FIGS. 8 and 10. The O-ring 126 may be located near the base of the hub 108 as illustrated in FIG. 11. The hub conduit 122 and hub gap 124 may connect perpendicularly with the flow tube 104 and form a straight passageway to the nozzles of the spray cans 110 and/or to the heads 120 of the CIP module 116. In other words, the hub conduit 122 may contain no bends, corners, right angles, or other crevices as illustrated in FIG. 9.

The primary purpose of the gassing module 102 when coupled with the spray can delivery system 128 may be the addition of propellant to the food dispensing spray cans 110 in order to pressurize the cans. The propellants may include compressed gas propellants, such as nitrous oxide. The propellant may be pumped through the flow tube 104 from both directions 132 as illustrated in FIG. 1. The valve or valves 106 located between the hubs 108 may be opened. It is contemplated that other flow paths and directional flows that maintain enough pressure and correct direction may be utilized without departing from the scope and intent of the disclosure. Two valves 112 and 114 may be located between the hubs 108. The valves 112 and 114 may be located between sixteen hubs 108 with eight hubs positioned between valve 112 and 114 and four hubs positioned on the other sides of both valves 112 and 114 as illustrated in FIGS. 1 through 3. With the valve or valves 106 open, the propellant may flow 132 freely from both sides of the flow tube 104 until the two flows of propellant meet in the center of the flow tube 104. The pressure created by the meeting of the two streams of propellant may push the propellant through the hubs 108 towards the spray cans 132.

The propellant may be directed 132 through the hub conduit 122 and hub gap 124 of the hubs 108 to the spray cans 110 as illustrated in FIG. 1. Again the hub conduit 122 may create a straight passageway to the hub gap 124 as illustrated in FIG. 9. The propellant may enter the cans by pushing on the nozzles of the spray cans 110 with enough pressure to compress the nozzles' springs, opening the nozzles and allowing propellant to enter the spray cans 110. When the desired amount of propellant is within the spray cans 110, the spray can delivery system 128 may be released from the gassing module which relieves the pressure on the spray can nozzles, which stops the propellant flow through the flow tube 104 and hubs 108. The spray can inserted propellant, such as nitrous oxide, may exude pressure on the food product as the spray cans' springs decompress on the nozzles' openings with the reduction in pressure and possibly excretes a bit of the food product from the pressurize spray cans 110 into the gassing module 102 before the springs fully tighten to close the nozzles of the spray cans 110, thus creating the need for cleaning It is contemplated that other mechanisms that effectively close pressurized spray cans besides spring seals may be utilized without departing from the scope and spirit of the disclosure.

Prior to cleaning, the nozzles of the spray cans 110 may be removed from the gassing module 102 by the gassing module 102. The clean in place module 116 may then automatically connect its heads 120 into the hubs 108 of the gassing module 102. In order for the clean in place system to clean the gassing module 102 effectively, the cleaning solution must be manipulated to flow through all of the hubs 108. Moreover, a minimum flow rate and minimum velocity determined based on pipe diameters must be met or exceeded for the flow tube 104, hubs 108, clean in place module heads 120, and clean in place module receptacle tubes 118. Area multiplied by velocity equals volumetric flow rate. Flow rate for a cylinder is determined by the following equation: $(\Pi r^2)(v)$=Flow rate (where $\Pi$ is the ratio of a circle's circumference divided by its diameter, r is the radius of a circle, $\Pi r^2$ is the area of a circle, and v is velocity). Velocity is the rate at which an object changes position. Velocity may be calculated by dividing displacement by time. Area is the extent of a two-dimensional surface enclosed within a boundary measured in square units.

A pump may push the liquid at a determined pressure. The amount of pressure utilized may effect volumetric flow rate and hence the starting velocity of the liquid. However, only certain amounts of velocity are possible at different diameters based on currently available suitable pumps. The smaller the diameter of a pipe, the more pressure required for effective cleaning, which becomes more difficult for the pump and piping.

The necessary flow rate and velocity for effective cleaning increases as radii and/or areas increase. Similarly, as radii and areas decrease so too does the minimum flow rate and necessary velocity for effective cleaning. The minimum flow rate insures that all the surfaces of an orifice, a pipe, and/or tube within the gassing module 102 that can be contaminated by food come into effective contact with the cleaning solution, which is pumped through the gassing manifold 100 to disinfect the gassing module 102 and may prevent the growth of potentially harmful microorganisms. A machine may be effectively cleaned by the clean in place system, when the machine is considered safe for utilization with food products for human consumption based on microorganism growth. If a pipe's diameter ranges from about 1 inch to about 2.9 inches, the recommended minimum velocity required for effective cleaning may range from about 5 feet per second to about 15 feet per second and the minimum flow rate would range from about 9.25 gallons per minute (1 inch pipe, 5 feet per second) to about 206 gallons per minute (2.9 inch pipe, 10 feet per second). If a pipe's diameter ranges from about 3 inches to about 3.9 inches the minimum velocity required for effective cleaning may range from about 6 feet per second to about 10 feet per second and the minimum flow rate would range from about 132 gallons per minute (3 inch pipe, 6 feet per second) to about 372 gallons per minute (3.9 inch pipe, 10 feet per second). If a pipe's diameter is about 4 inches or larger the minimum velocity required for effective cleaning may range from about 7 feet per second to about 15 feet per second and the minimum flow rate may range from about 274 gallons per minute (4 inch pipe, 7 feet per second) to about 588 gallons per minute (4 inch pipe, 15 feet per second).

Typically, pumped liquid will take the path of least resistance. If the valve or valves 106 of the gassing module 102 coupled with the CIP module 116 of FIG. 3 were opened when liquid was pumped in one direction with a higher pressure through the flow tube 104, then most of the pumped liquid may continue straight through the flow tube 104 and exit the gassing module 102 with very little if any of the pumped liquid flowing through the hubs 108. Furthermore, any liquid that passes through the hubs 108 to the heads 120 and receptacle tubes 118 of the CIP module 116 may not have enough pressure or force to exit the receptacle tubes 118 and will simply accumulate. Moreover, the velocity of the liquid traveling through the different hubs 108 and receptacle tube 118 may have differing velocities based on the amount of pressure each stream is under.

Therefore, to prevent a substantial pressure drop in the gassing module and to ensure that all of the hubs receive an effective amount of cleaning fluid, the flow of the cleaning solution may be channeled. The valve or valves 106 located between the hubs 108 may be closed. The valves 112 and 114 may be closed. The gassing module 102 may then pump with the necessary pressure the cleaning solution, such as solvents, in one end of the flow tube 104. The liquid may move in one direction 134 through the flow tube 104 and out the other side as illustrated in FIG. 2, unlike the propellant that is pumped in from both sides 132. The closed valve or valves may manipulate and direct the flow 134 of the cleaning solution. The closed valve or valves 106 may put a substantial amount of pressure on the pumped cleaning solution, which pushes the liquid through the hubs 108 towards the CIP module. The pressure may decrease from left to right in FIG. 2 along the flow path 134. Valves 112 and 114 provide enough back pressure to force the flow from the gasser module 102 through the CIP module 116. Velocity may remain relatively constant through the entire system because the areas change to accommodate the pressure differences.

The cleaning solution may enter the flow tube 104 from one side of the gassing module 102 and then hit the closed valve or valves 106. The closed valve or valves 106 may cause the cleaning solution to be pushed towards the CIP module 134 through the hubs 108 before the closed valve 106 as illustrated in FIG. 2. The valve or valves 106 may be positioned to channel the cleaning solution to flow 134 in one direction through the flow tube 104 of the gassing module 102. The liquid may proceed through the hubs 108 to the heads 120 of the clean in place module 116. Next, the cleaning solution may flow 134 to the receptacle tubes 118 of the CIP module 116 until the liquid reaches the end of the receptacle tubes 118, which may force the cleaning solution up through the heads 120 of the clean in place module 116 that are located down stream from the already encountered closed valve 106 of the gassing module 102 as illustrated in FIG. 2. The ending of the receptacle tube 118 of the CIP module 116 may create enough pressure to pump the cleaning solution not only back through heads 102 farther downstream, but may also cause the cleaning solution to flow 134 back through different hubs 108 farther downstream and into the flow tube 104. The cleaning solution may either exit the module from the flow tube 104 at this point or continue to travel through the flow tube 104 until the cleaning solution contacts another closed valve 106 causing the liquid to flow 134 through a select number of hubs prior to the closed valve 106 and repeat the previously described flow pattern again with cleaning solution existing the flow tube at then end of this flow pattern.

The cleaning solution may flow 134 from one end of the flow tube 104 in one direction to the other end of the flow tube 104 and flow through the hubs 108 and heads 120 in sections of four as illustrated in FIG. 2. It is understood that other different correlating configurations of hubs, spray cans, valves, and heads may be utilized without departing from the scope and spirit of the disclosure. The gassing module may have only one valve with eight or six total hubs split evenly on either side of the valve. The gassing module may also have more or fewer than 8 hubs.

The velocity of the cleaning solution pumped through multiple tubes with multiple bends may change based on the amount of pressure the liquid is under at the inlet to the gassing module 102. The more turns and/or corners the liquid flows through, the greater the pressure drop. The velocity of the cleaning solution may vary as it travels from the flow tube 104 through different hubs 108 as described above, but the liquid is prevented from falling below the minimum velocity and the minimum flow rate required for the diameters and enclosed two-dimensional surfaces at issue in the gassing module and the CIP module.

To accomplish this, the hubs 108 may be modified to create fewer bends and turns. However, this change alone will not maintain a minimum flow rate. In order to achieve the minimum flow rate, based on the equation above, the area of the tubes, pipes, orifices, and other surfaces of the coupled gassing module and CIP module that the cleaning solution flows through may be designed to counter act any anticipated change in velocity. By changing the area of each portion of the coupled gassing module and CIP module that the cleaning solution flows through based on the necessary velocity needed in a certain position and at all of the downstream positions, a minimum flow rate and velocity may be achieved with the newly calculated and precisely implemented diameters and enclosed two-dimensional surfaces to create a clean in place gassing manifold 100.

Therefore, in order to maintain a minimum flow rate when the gassing module and CIP module are coupled, the flow tube's 104, the hub conduit's 122, the hub gap's 124, the CIP module heads' 120, and the CIP module receptacle tubes' 118 necessary areas may be calculated and precisely implemented into the CIP module and the gassing module. The total area of the receptacle tube 118 may vary depending upon which hubs the receptacle tube is closest too. The portion of the receptacle tube 118 near the hubs 108 farthest away from the closed valve or valves 106 may be smaller than portions of the receptacle tube near the hubs 108 closest to the closed valve or valves 106.

Similarly, the total area of the hub conduit 122 may be smaller in the hubs position farther away from the closed valve or valves 106 and may be larger in the hubs 108 positioned closest to the closed valve or valves 106. Moreover, the area of the hub gap 122 around the head 120 of the CIP module 116 above the O-ring 126 may be equal to the area of the hub conduit 122 in order to maintain the necessary flow rate. The area of the hub gap 122 around the head 120 of the CIP module 116 above the O-ring 126 may be the extent of the two-dimensional surface enclosed within those boundaries as measured in square units.

The hubs 108, however, still have to easily and automatically fit over the nozzles of the spray cans 110. Therefore, the hubs 108 may be designed to taper enough prior to or after the O-ring 126 to allow the nozzles of the spray cans 110 to be inserted into the hubs 108 automatically by the gassing module 102 but created small enough past the O-ring 126 to have an area above the O-ring in the hub gap 124 around head 120 of the CIP module 116 that is equivalent to the area of the hub conduit 122 to maintain velocity and exceed or meet the minimum flow rate and velocity of the cleaning solution.

By implementing set areas at calculated points, the minimum flow rate may be achieved or exceeded by the cleaning solution to effectively clean the gassing module of the CIP gassing manifold 100. Different effective flow rates and velocities for clean in place systems may be achieved by combining different areas and different starting pressures for the cleaning solution to effectively clean a gassing manifold for a food product distributed in a pressurized spray can.

Previously utilized gassing manifolds did not lend themselves easily to clean in place systems. Several problems had to be overcome to design a clean in place system for a gassing manifold. The radius of a flow tube of a typical gassing module was too small to maintain the necessary flow rates and velocities for an effective clean in place system. Also, the hub conduits of typical gassing modules did not have straight passageways to the hub gaps or their cross sectional areas were not consistent to allow consistent velocities. The hub conduits of typical gassing modules contained at least one corner and/or right angle and may have varied in area and/or radii. In a specific gassing modules, the hub conduits utilize a five way cross connection to enter the hub gap, which may reduce pressure and create variable velocities. Additionally, the hub gap's area needed to be large enough to allow the hub to be automatically inserted over the nozzle of the spray cans by the gassing module while still reaching or exceeding the minimum flow rate and velocity. These features prevented a minimum flow rate and velocity from being obtained or exceeded and could prevent the cleaning solution from flowing in the intended and/or desired direction.

A sanitary clamp 130 may be utilized to secure the different modules to their support structures as illustrated in FIGS. 3, 7, and 8. Typical modules of previously made gassing manifolds were attached to supporting structures by utilizing screws and other attachment mechanisms that create spaces for food particle lodgment, which again create threads and separate parts that need to be disassembled for effective cleaning Threads and the need to disassemble the gassing module for proper cleaning may be eliminated by utilizing sanitary clamps 130 that prevent food particles from gaining access to crevasses.

Currently, gassing manifolds are cleaned about once a day to disinfect their gassing modules and to prevent the growth of harmful microorganisms. Often times, to clean one type of a current gassing module, the hubs are manually unscrewed and cleaned and/or soaked for effective cleaning In another type of current gassing module, the module is one continuous structure with hubs that are not detachable. In this current configuration, the areas of the tubes, pipes, and orifices are not regulated and a CIP system is not possible, because enormous pressure drops would occur when a cleaning solution is pumped through this type of gassing module. Therefore, these types of current gassing modules are manually removed from their supporting structures and soaked for effective cleaning Eliminating the need for manual labor and soakings, drastically decreases cleaning time and increases cleaning consistency by allowing a CIP system to automatically clean the gassing module with minimal human involvement.

Referring to FIG. 12 a method for providing a clean in place gassing manifold 200 is shown. Method 200 provides a gassing manifold for alternately coupling a gassing module and a complementary clean in place module, 202. Method 200 couples the complementary clean in place module with the gassing module to form a clean in place system, 204.

Referring to FIG. 13 another method for providing a clean in place gassing manifold 300. Method 300 provides a gassing module comprising a hub, the gassing module and the hub being formed as a unitary device, 302. Method 300 provides a complementary clean in place module for coupling the gassing module, the complementary clean in place module comprising a head that inserts into the hub of the gassing module, 304. The gassing module coupled with the complementary clean in place module allows a cleaning solution to be pumped through the coupled modules at and above a minimum flow rate and a minimum velocity for effective cleaning. Furthermore, the hub may be designed and built to create a straight passageway from the flow tube of the gassing module to the head of the clean in place module and may be designed to include a hub conduit with an area equal to the area of the hub gap above the O-ring when the head of the complementary clean in place module is inserted into gassing module. Additionally, the clean in place module and the gassing module may be attached to their supporting structures by utilizing a sanitary clamp.

Figure 14:
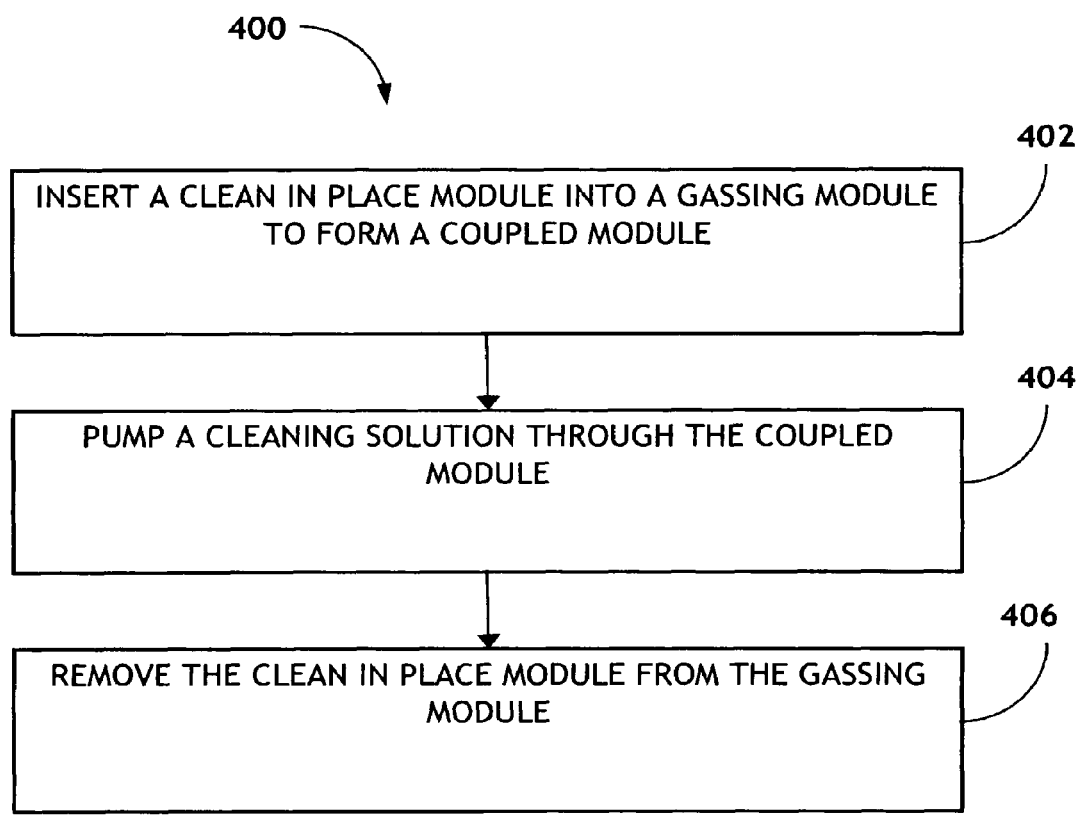
FIG. 14 is diagram illustrating a method for cleaning a gassing manifold.

Referring to FIG. 14 a method for cleaning a gassing manifold 400 is shown. Method 400 inserts a clean in place module into a gassing module to form a coupled module, 402. Method 400 pumps a cleaning solution through the coupled module, 404. Method 400 removes the clean in place module from the gassing module, 406. The coupled module allows the cleaning solution to be pumped through the coupled module at and above a minimum flow rate and a minimum velocity for effective cleaning.

EXAMPLE 1

The gassing module contained 16 hubs. Eight of these hubs are positioned between two valves with the remaining eight hubs split evenly on the other sides of both valves as illustrated in FIG. 2. The complementary clean in place module, when coupled with the gassing module, allowed the cleaning solution to travel thorough the coupled modules at velocities of five feet per second and above. The diameter of the flow tube ranged from about 0.4 inches to about 0.6 inches. The diameter of the hub conduits ranged from about 0.12 inches to about 0.25 inches. The area of the hub gap above the O-ring when the head of the CIP module is inserted into the hub gap is equivalent to the area of the hub conduit. The heads of the CIP module ranged in diameter from about 0.3 inches to about 0.4 inches. The receptacle tubes of the CIP module ranged in diameter from about 0.31 inches to about 0.5 inches. The cleaning solution is pumped through the module with a pressure ranging from about 20 to about 60 pounds per square inch. In this configuration, the resulting CIP manifold had a flow rate that effectively cleans the gassing module.

EXAMPLE 2

The gassing module contained 2 hubs. One valve is positioned between the two hubs. All conduits within the gassing module and CIP module including the flow tube and receptacle tubes had diameters of 0.125 inches. The area of the hub gap above the O-ring when the head of the CIP module was inserted into the hub gap was equivalent to the area of the hub conduit. The cleaning solution was pumped through the coupled gassing module and CIP module with a closed valve at two different flow rates. First, the cleaning solution was pumped through the coupled gassing module and CIP module with a closed valve at a flow rate of 3 feet per second (0.11 gallons/min). The pressure drop range within the coupled gassing module and CIP module with a closed valve ranged from 1.6 psi to about 15 psi. Next, a flow rate of 15 feet per second (0.58 gallon/min) was utilized resulting in a pressure drop range of about 25 psi to about 50 psi.

EXAMPLE 3

The gassing module contained 2 hubs. One valve is positioned between the two hubs. All conduits within the gassing module and CIP module including the flow tube and receptacle tubes had a diameter of 1.25 inches. The area of the hub gap above the O-ring when the head of the CIP module was inserted into the hub gap was equivalent to the area of the hub conduit. The cleaning solution was pumped through the coupled gassing module and CIP module with a closed valve at two different flow rates. First, the cleaning solution was pumped through the coupled gassing module and CIP module with a closed valve at a flow rate of 3 feet per second (11.5 gallons/min). The pressure drop range within the coupled gassing module and CIP module with a closed valve ranged from 0.2 psi to about 8 psi. Next, a flow rate of 15 feet per second (57 gallon/min) was utilized resulting in a pressure drop range of about 4 psi to about 18 psi.

It should be noted that based on EXAMPLES 2 and 3, as tube diameter increases from 0.125 inches to 1.25 inches, the pressure drop range may decrease helping to maintain a desired velocity. Also, as the flow rate increases so does the pressure drop range. Therefore, in order to achieve the desired flow rate and velocity the size of the conduits and the flow rate may need to be adjusted in relation to each other.

EXAMPLE 4

The gassing module contained 32 hubs and 4 valves. Four hubs are present on each end of the gassing module before a valve is reached. Eight hubs were found between these two valves and the next interior hubs leaving eight hubs between the most two interior hubs. All conduits within the gassing module and CIP module including the flow tube and receptacle tubes had a diameter of 0.125 inches. The area of the hub gap above the O-ring when the head of the CIP module was inserted into the hub gap was equivalent to the area of the hub conduit. The cleaning solution was pumped through the coupled gassing module and CIP module with closed valves at two different flow rates. First, the cleaning solution was pumped through the coupled gassing module and CIP module with closed valves at a flow rate of 3 feet per second (0.11 gallons/min). The pressure drop range within the coupled gassing module and CIP module with closed valves ranged from 8 psi to about 23 psi. Next, a flow rate of 15 feet per second (0.58 gallon/min) was utilized resulting in a pressure drop range of about 150 psi to about 250 psi.

EXAMPLE 5

The gassing module contained 32 hubs and 4 valves. Four hubs are present on each end of the gassing module before a valve is reached. Eight hubs were found between these two valves and the next interior hubs leaving eight hubs between the two most interior hubs. All conduits within the gassing module and CIP module including the flow tube and receptacle tubes had a diameter of 1.25 inches. The area of the hub gap above the O-ring when the head of the CIP module was inserted into the hub gap was equivalent to the area of the hub conduit. The cleaning solution was pumped through the coupled gassing module and CIP module with closed valves at two different flow rates. First, the cleaning solution was pumped through the coupled gassing module and CIP module with closed valves at a flow rate of 3 feet per second (11.5 gallons/min). The pressure drop range within the coupled gassing module and CIP module with closed valves ranged from 2 psi to about 20 psi. Next, a flow rate of 15 feet per second (57 gallon/min) was utilized resulting in a pressure drop range of about 15 psi to about 60 psi.

It should be noted that based on EXAMPLES 4 and 5, as tube diameter increases from 0.125 inches to 1.25 inches, the pressure drop range may decrease helping to maintain a desired velocity. Also, as the flow rate increases so does the pressure drop range. Therefore, in order to achieve the desired flow rate and velocity the size of the conduits and the flow rate may need to be adjusted in relation to each other.

Furthermore, based on EXAMPLES 2 through 5, as the number of hubs increases so too does the pressure drop range showing that as the number of turns and corners increase, the harder it is to prevent pressure drops. Therefore, the desired flow rate and velocity may depend on the conduit size, the flow rate, and the number of bends, twists, and turns found within the coupled gassing module and CIP module.

EXAMPLE 6

The microbiological growth in the gassing module was tested after utilizing the clean in place system. The clean in place system utilized was identical to the system shown in FIG. 2. Three different runs were conducted in this experiment.

In the first run no food was inserted into the gassing module. One swab was taken for two hubs for each of the 16 hubs resulting in 8 swabs and a swab was taken at the gasser port, the incoming end of the module, and the outgoing end of the module to test for the microbiological count and utilized as the control samples. Next, the clean in place system was utilized. The CIP module was coupled to the gassing module and the valves closed. The pump was set at 40 psi with a flow rate of about 3.50 gallons per minute to about 3.75 gallons per minute. A cold rinse was run through the system for five minutes followed by a hot rinse for 10 minutes, a caustic rinse for 30 minutes and a final rinse for 15 minutes. The caustic rinse may comprise 2.5% NaOH heated with steam. After this process, one swab was taken for two hubs for each of the 16 hubs resulting in 8 swabs and a swab was taken at the gasser port, the incoming end of the gassing module, and the outgoing end of the gassing module to test for the microbiological count. As a guideline, a reading anywhere under 5,000 is acceptable. The control swab for this test had a count of 1,895, while only the swabs at hubs 3 and 4; 15 and 16; and the incoming end of gassing module had any count after the clean in place system was utilized. Hubs 3 and 4 had a count of 235. Hubs 15 and 16 had a count of 58 and the incoming end of the gassing module had a count of 862, which are all less than the 5,000 guideline.

In the second run, non-dairy whipped cream was run through the gassing module. Next, the outside hubs were sprayed by a Strahman hot water hose. The Strahman hot water hose is produced by Strahman Valves, Inc. located at 2801 Baglyos Circle, Lehigh Valley Industrial Park VI, Bethlehem, Pa. 18020. The control sample was taken in this experiment after spraying the hubs with the Strahman hot water hose. The control sample consisted of one swab taken for two hubs for each of the 16 hubs resulting in 8 swabs and a swab was taken at the gasser port, the incoming end of the gassing module, and the outgoing end of the gassing module to test for the microbiological count. The control reading had a count of 116,087. The clean in place system utilized a pump set at 55 psi with a flow rate of about 4.25 gallons per minute to about 4.75 gallons per minute. Again, a cold rinse was ran through the system for five minutes followed by a hot rinse for 10 minutes, a caustic rinse for 30 minutes and a final rinse for 15 minutes. After utilizing the clean in place system all of the swabs were well less than 5,000 and more specially, all the swabs were less than 1400. Moreover, six of the hubs and the outgoing end of the gassing module registered zero counts.

In the final run, the gassing module was filled with whipped cream and left to sit for about 5 hours to dry. Again, the outside hubs were sprayed by a Strahman hot water hose. After this period, one swab was taken for two hubs for each of the 16 hubs resulting in 8 swabs and a swab was taken at the gasser port, the incoming end of the gassing module, and the outgoing end of the gassing module to test for the microbiological count and utilized as the control samples. The control sample had a microbiological count of 16,760. Next, the clean in place system was utilized. The CIP module was coupled to the gassing module and the valves closed. The pump was set at 55 psi with a flow rate of about 5.00 to about 5.50. A cold rinse was ran through the system for five minutes followed by a hot rinse for 10 minutes, a caustic rinse for 40 minutes and a final rinse for 15 minutes. After utilizing the clean in place system all of the swabs had a microbiological count of 0.

Therefore, this experiment illustrates the effectiveness of the clean in place system for cleaning the gassing module by showing that after cleaning all of the microbiological counts were less than the guideline, which requires a count of less than 5,000. Moreover, this experiment fully covered the gassing module with food, whereas in actual use, typically, only 25% of the gassing module will be contacted with food. Therefore, when utilized in production, it is contemplated that the clean in place system may be even more effective, because there would be less microbiological growth to kill than found in previously described second and third runs.

The methods disclosed may be implemented as sets of instructions, through a single production device, and/or through multiple production devices. Further, it is understood that the specific order or hierarchy of steps in the methods disclosed are examples of exemplary approaches. Based upon design preferences, it is understood that the specific order or hierarchy of steps in the method can be rearranged while remaining within the scope and spirit of the disclosure. The accompanying method claims present elements of the various steps in a sample order, and are not necessarily meant to be limited to the specific order or hierarchy presented.

It is believed that the disclosure and many of its attendant advantages will be understood by the foregoing description, and it will be apparent that various changes may be made in the form, construction and arrangement of the components thereof without departing from the scope and spirit of the disclosure or without sacrificing all of its material advantages. The form herein before described being merely an explanatory, it is the intention of the following claims to encompass and include such changes.

What is claimed is:

1. A method, comprising:
engaging a complementary clean in place module with a gassing module, the gassing module operable to add a propellant gas to a spray can, the gassing module including a hub configured to receive a nozzle of the spray can and including a seal configured to seal the hub to the nozzle when the nozzle is received in the hub, the complementary clean in place module including a head configured to be inserted in the hub so that the hub is sealed to the head by the seal;
injecting a cleaning solution through the gassing module, wherein the head is configured to receive the cleaning fluid injected through the gassing module to at least partially clean the gassing module.

2. The method of claim 1, wherein the gassing module further comprises a supporting structure configured to support the gassing module and a sanitary clamp configured to attach the gassing module to the supporting structure.

3. The method of claim 1, wherein a microbiological count of less than 5,000 is found within any portion of the gassing module after the cleaning fluid is injected through the gassing module.

4. The method of claim 1, wherein the gassing module further comprises a flow tube configured to provide a supply of propellant gas to the hub.

5. The method of claim 4, wherein the hub further comprises a hub gap, the hub gap configured to receive the nozzle of the spray can when the nozzle is inserted in the hub and the head when the head is inserted in the hub, the hub gap including the seal.

6. The method of claim 5, wherein the gassing module further comprises a hub conduit configured to port the flow tube to the hub gap.

7. The method of claim 6, wherein the seal comprises an O-ring.

8. The method of claim 7, wherein an enclosed two-dimensional surface of the hub gap above the O-ring has an area equal to an area of the hub conduit to maintain a flow rate of the cleaning fluid through the hub.

9. The method of claim 6, wherein:
the flow tube has a diameter of about 0.4 inches to about 0.6 inches;
the hub conduit has a diameter of about 0.12 inches to about 0.25 inches; and
the head has a diameter of about 0.3 inches to about 0.4 inches.

10. The method of claim 9, wherein the complementary clean in place module includes a receptacle tube, the receptacle tube having a diameter of about 0.31 inches to about 0.5 inches, wherein the cleaning solution is pumped at about 20 pounds per square inch to about 60 pounds per square inch, and wherein the cleaning solution maintains a flow rate of at least 5 feet per second.

11. A method for cleaning a gassing manifold, comprising:
inserting a clean in place module into a gassing module to form a coupled module;
pumping a cleaning solution from the clean in place module into the gassing module; and
removing the clean in place module from the gassing module,
wherein the coupled module allows the cleaning solution to be pumped from the clean in place module into the gassing module at and above a minimum flow rate and a minimum velocity for effective cleaning.

12. The method of claim 11, wherein a microbiological count of less than 5,000 is found within any portion of the gassing module after pumping the cleaning solution from the clean in place module into the gassing module at and above the minimum flow rate and the minimum velocity.

13. A method for cleaning a gassing manifold, comprising:
providing a gassing module comprising a hub, the gassing module and the hub being formed as a unitary device; and
providing a complementary clean in place module for coupling the gassing module, the complementary clean in place module comprising a head that inserts into the hub of the gassing module,
pumping a cleaning solution from the clean in place module into the gassing module at and above a minimum flow rate and a minimum velocity for effective cleaning.

14. The method of claim 13, wherein the gassing module includes a supporting structure that is attached to the gassing module by utilizing a sanitary clamp.

15. The method of claim 13, wherein a microbiological count of less than 5,000 is found within any portion of the gassing module after the cleaning solution is pumped from the clean in place module into the gassing module at and above the minimum flow rate and the minimum velocity.

16. The method of claim 13, wherein the hub includes a hub conduit and a hub gap.

17. The method of claim 16, wherein the hub conduit is a straight passageway.

18. The method of claim 17, wherein the hub gap includes an O-ring.

19. The method of claim 18, wherein an enclosed two-dimensional surface of the hub gap above the O-ring has an area equal to an area of the hub conduit.

20. The method of claim 16, further comprising:
the gassing module comprising,
a flow tube having a diameter of about 0.4 inches to about 0.6 inches,
the hub conduit having a diameter of about 0.12 inches to about 0.25 inches, and
the clean in place module comprising,
a head having a diameter of about 0.3 inches to about 0.4 inches, and
a receptacle tube having a diameter of about 0.31 inches to about 0.5 inches; and
the cleaning solution pumped at about 20 pounds per square inch to about 60 pounds per square inch from the clean in place module into the gassing module,
wherein the cleaning solution maintains a flow rate of at least 5 feet per second.

* * * * *